United States Patent
Andrews et al.

[11] Patent Number: 5,910,101
[45] Date of Patent: Jun. 8, 1999

[54] DEVICE FOR LOADING AND CENTERING A VASCULAR RADIATION THERAPY SOURCE

[75] Inventors: Christopher C. Andrews, Murrieta; Paul V. Neale, San Diego, both of Calif.

[73] Assignee: Advanced Cardiovascular Systems, Inc., Santa Clara, Calif.

[21] Appl. No.: 08/705,574

[22] Filed: Aug. 29, 1996

[51] Int. Cl.$^6$ .................................................. A61N 5/00
[52] U.S. Cl. .................................................. 600/3
[58] Field of Search ................................. 600/1–8

[56] References Cited

U.S. PATENT DOCUMENTS

| | | |
|---|---|---|
| 4,697,575 | 10/1987 | Horowitz . |
| 4,706,652 | 11/1987 | Horowitz . |
| 4,762,130 | 8/1988 | Fogarty et al. . |
| 4,763,671 | 8/1988 | Goffinet . |
| 4,815,449 | 3/1989 | Horowitz . |
| 4,861,520 | 8/1989 | van't Hooft et al. . |
| 4,969,863 | 11/1990 | van't Hooft et al. . |
| 4,983,167 | 1/1991 | Sahota . |
| 5,002,560 | 3/1991 | Machold et al. . |
| 5,015,230 | 5/1991 | Martin et al. . |
| 5,032,113 | 7/1991 | Burns . |

(List continued on next page.)

FOREIGN PATENT DOCUMENTS

| | | |
|---|---|---|
| 0 633 041 A1 | 1/1995 | European Pat. Off. . |
| 0 688 580 A1 | 12/1995 | European Pat. Off. . |
| 91 02 312 | 6/1992 | Germany . |
| 4315002 | 5/1993 | Germany . |
| WO 93/04735 | 3/1993 | WIPO . |
| WO 94/25106 | 11/1994 | WIPO . |
| WO 95/19807 | 7/1995 | WIPO . |
| WO 95/26681 | 10/1995 | WIPO . |
| WO 96/06654 A1 | 3/1996 | WIPO . |
| WO 96/10436 | 4/1996 | WIPO . |
| WO 96/14898 A1 | 5/1996 | WIPO . |

OTHER PUBLICATIONS

Lindsay, et al., Aortic Arteriosclerosis In The Dog After Localized Aortic X–Irradiation, *Circulation Research*, vol. X, Jan. 1964.

Friedman, et al., The Antiatherogenic Effect of Iridium$^{92}$ Upon The Cholesterol–Fed Rabbit, *Journal of Clinical Investigation* (1964).

Friedman, et al., Effect of Iridium 192 Radiation On Thromboatherosclerotic Plaque In the Rabbit Aorta, *Arch Path*, vol. 80, Sep. 1965.

Hoopes, et al., Intraoperative Irradiation Of The Canine Abdominal Aorta And Vena Cava, *Journal of Radiation Oncology*, vol. 13 (1987).

Dawson, Theoretic Considerations Regarding Low–Dose Radiation Therapy For Prevention Of Restenosis After Angioplasty, *Texas Heart Institute Journal*, Vo.. 18, No. 1 (1991).

(List continued on next page.)

*Primary Examiner*—John P. Lacyk
*Attorney, Agent, or Firm*—Fulwider Patton Lee & Utecht, LLP

[57] ABSTRACT

An intravascular catheter having an expandable inflation region adapted for centering a radiation dose in a body lumen for a period of time sufficient to permit delivery of a radiation dose to the body lumen. The catheter includes a delivery lumen, and a blind internal lumen for receiving a wire having a radiation source located at the distal end of the wire. The blind internal lumen is received in the delivery lumen of the catheter. The blind internal lumen prevents contamination of the radiation source by fluids from the body lumen. The radiation source is advanced through the blind internal lumen towards the inflation region of the catheter. The inflation region includes a plurality of balloon lobes at the distal end of the catheter. The plurality of balloon lobes, when inflated, can center the radiation source within a curved section of the body lumen.

18 Claims, 3 Drawing Sheets

U.S. PATENT DOCUMENTS

| | | |
|---|---|---|
| 5,034,001 | 7/1991 | Garrison et al. . |
| 5,059,166 | 10/1991 | Fischell et al. . |
| 5,180,368 | 1/1993 | Garrison . |
| 5,199,939 | 4/1993 | Dake et al. . |
| 5,213,561 | 5/1993 | Weinstein et al. . |
| 5,263,963 | 11/1993 | Garrison et al. . |
| 5,295,959 | 3/1994 | Gurbel et al. . |
| 5,295,960 | 3/1994 | Aliahmad et al. . |
| 5,295,995 | 3/1994 | Kleiman . |
| 5,302,168 | 4/1994 | Hess . |
| 5,306,246 | 4/1994 | Sahatjian et al. . |
| 5,308,356 | 5/1994 | Blckshear, Jr. et al. . |
| 5,334,154 | 8/1994 | Samson . |
| 5,350,361 | 9/1994 | Tsukashima et al. . |
| 5,352,199 | 10/1994 | Tower . |
| 5,354,257 | 10/1994 | Roubin et al. . |
| 5,395,333 | 3/1995 | Brill . |
| 5,411,466 | 5/1995 | Hess . |
| 5,456,667 | 10/1995 | Ham et al. . |
| 5,458,572 | 10/1995 | Campbell et al. . |
| 5,484,384 | 1/1996 | Fearnot . |
| 5,503,613 | 4/1996 | Weinberger . |
| 5,503,614 | 4/1996 | Liprie . |
| 5,540,659 | 7/1996 | Tierstein ................................ 600/3 |
| 5,643,171 | 7/1997 | Bradshaw et al. ...................... 600/3 |
| 5,730,698 | 3/1998 | Fischell et al. . |

OTHER PUBLICATIONS

Schwartz, et al., Effect Of External Beam Irradiation On Neointimal Hyperplasia After Experimental Coronary Artery Injury, *JACC*, vol. 19, No. 5 (Apr. 1992).

Wiedermann, et al., Intracoronary Irradiation Markedly Reduces Restenosis After Balloon Angioplasty In A Porcine Model, *JACC*, vol. 23, No. 6 (1994).

Fischell, et al., Low–Dose β–Particle Emmission From 'Stent' Wire Results In Complete, Localized Inhibition Of Smooth Muscle Cell Proliferation, *Basic Science Reports* (1994).

Waksman, et al., Endovascular Low–Dose Irradiation Inhibits Neointima Formation After Coronary Artery Balloon Injury In Swine—A Possible Role For Radiation Therapy In Restenosis Prevention, *Circulation*, vol. 91, No. 5 (Mar. 1, 1995).

Weshler, et al., Inhibition By Irradiation Of Smooth Muscle Cell Proliferation In The De–Endothelialized Rat Aorta, *Frontiers of Radiation Biology* (1988).

Hehrlein, et al., Radioactive Stents, *Discoveries in Radiation for Restenosis*, Abstract 22 (Jan. 1996).

Fischell, et al., A Beta–Particle Emitting Radioisotope Stent For The Prevention Of Restenosis, *Discoveries in Radiation for Restenosis*, Abstract 23 (Jan. 1996).

Li, et al., A Novel Brachyehtapy Source For Treatment of Coronary Artery Restenosis, *Discoveries in Radiation for Restenosis*, Abstract 24 (Jan. 1996).

Waksman, Catheter–Based Radiation In Stented Arteries, *Discoveries in Radiation for Restenosis*, Abstract 25 (Jan. 1996).

Martin, Radiation For Peripheral Applications: Technical Aspects, *Discoveries in Radiation for Restenosis*, Abstract 27 (Jan. 1996).

Lumsden, et al., Restenosis In Peripheral Vascular Disease, *Discoveries in Radiation for Restenosis*, Abstract 28 (Jan. 1996).

Schopohl, et al., Endovascular Irradiation For Avoidance of Recurrent Stenosis After Stent Implantation in Peripheral Arteries—5 Years Follow–Up, *Discoveries in Radiation for Restenosis*, Abstract 29 (Jan. 1996).

Waksman, Radiation In the Peripheral System At Emory, *Discoveries in Radiation for Restenosis*, Abstract 30 (Jan. 1996).

Teirstein, et al., Catheter–Based Radiation Therapy To Inhibit Restenosis Following Coronary Stenting, *Discoveries in Radiation for Restenosis*, Abstract 31 (Jan. 1996).

King, Clinical Restenosis Trials Using Beta Energy Radiation, *Discoveries in Radiation for Restenosis*, Abstract 32 (Jan. 1996).

Urban, et al., Endovascular Irradiation With 90Y Wire, *Discoveries in Radiation for Restenosis*, Abstract 33 (Jan. 1996).

Condado, et al., Late Follow–Up After Percutaneous Transluminal Coronary Angioplasty (PTCA) And Intracoronary Radiation Therapy (ICRT), *Discoveries in Radiation for Restenosis*, Abstract 34 (Jan. 1996).

Weldon, Catheter Based Beta Radiation System, *Discoveries in Radiation for Restenosis*, Abstract 35 (Jan. 1996).

van't Hooft, et al., HDR Afterloader For Vascular Use, *Discoveries in Radiation for Restenosis*, Abstract 36 (Jan. 1996).

Fischell, et al., The Radioisotope Stent: Conception And Implementation, *Discoveries in Radiation for Restenosis*, Abstract 37 (Jan. 1996).

Popowski, et al., Radioactive Wire In A Self–Centering Catheter System, *Discoveries in Radiation for Restenosis*, Abstract 38 (Jan. 1996).

Calfee, High Dose Rate Afterloader System For Endovascular Use—Neocardia, *Discoveries in Radiation for Restenosis*, Abstract 39 (Jan. 1996).

Smith, Issues On Handling Radioactive Devices To Prevent Restenosis, *Discoveries in Radiation for Restenosis*, Abstract 40 (Jan. 1996).

Kuntz, et al., Generalized Model Of Restenosis After Conventional Balloon Angioplasty, Stenting And Directional Atherectomy, collected in *Discoveries in Radiation for Restenosis—Selected Literature* (Jan. 1996).

Schwartz, et al., Differential Neointimal Response to Coronary Artery Injury In Pigs And Dogs, collected in *Discoveries in Radiation for Restenosis—Selected Literature* (Jan. 1996).

Haude, et al., Quantitative Analysis Of Elastic Recoil After Balloon Angioplasty And After Intracoronary Implantation Of Balloon–Expandable Palmaz–Schatz Stents, collected in *Discoveries in Radiation for Restenosis—Selected Literature* (Jan. 1996).

Kakuta, et al., Differences In Compenstory Vessel Enlargement, Not Intimal Formation, Account For Restenosis After Angioplasty In The Hypercholesterolemic Rabbit Model, collected in *Discoveries in Radiation for Restenosis—Selected Literature* (Jan. 1996).

Unterberg, et al., Reduced Acute Thrombus Formation Results In Decreased Neointimal Proliferation After Coronary Angioplasty, collected in *Discoveries in Radiation for Restenosis—Selected Literature* (Jan. 1996).

Byhardt, et al., The Heart and Blood Vessels, collected in *Discoveries in Radiation for Restenosis—Selected Literature* (Jan. 1996).

Soares, et al., Measurement Of Radial Dose Distributions Around Small Beta Particle Emitters Using High Resolution Radiochromic Foil Dosimetry, collected in *Discoveries in Radiation for Restenosis—Selected Literature* (Jan. 1996).

Schwartz, et al., Effect Of External Beam Irradiation On Neointimal Hyperplasia After Experimental Coronary Artery Injury, collected in *Discoveries in Radiation for Restenosis—Selected Literature* (Jan. 1996).

Waksman, et al., Endovascular Low–Dose Irradiation Inhibits Neointima Formation After Coronary Artery Balloon Injury In Swine, etc., collected in *Discoveries in Radiation for Restenosis—Selected Literature* (Jan. 1996).

Wiedermann, et al., Intracoronary Irradiation Markedly Reduces Restenosis After Balloon Angioplasty In a Porcine Model, collected in *Discoveries in Radiation for Restenosis—Selected Literature* (Jan. 1996).

Wiedermann, et al., Intracoronary Irradiation Markedly Reduces Neointimal Proliferation After Balloon Angioplasty In Swine: Persistent Benefit At 6–Month Follow–Up, collected in *Discoveries in Radiation for Restenosis—Selected Literature* (Jan. 1996).

Wiedermann, et al., Effects of High–Dose Intracoronary Irradiation On Vasomotor Function And Smooth Muscle Histopathology, collected in *Discoveries in Radiation for Restenosis—Selected Literature* (Jan. 1996).

Waksman, et al., Intracoronary Low–Dose β–Irradiation Inhibits Neointima Formation After Coronary Artery Balloon Injury In The Swine Restenosis Model, collected in *Discoveries in Radiation for Restenosis—Selected Literature* (Jan. 1996).

March, et al., 8–Methoxypsoralen And Longwave Ultraviolet Irradiation Are A Novel Antiproliferative Combination For Vascular Smooth Muscle, collected in *Discoveries in Radiation for Restenosis—Selected Literature* (Jan. 1996).

Verin, et al., Intra–Arterial Beta Irradiation Prevents Neointimal Hyperplasia In a Hypercholesterolemic Rabbit Restenosis Model, collected in *Discoveries in Radiation for Restenosis—Selected Literature* (Jan. 1996).

Fischell, et al., Low–Dose, β–Particle Emmission Form 'Stent' Wire Results In Complete, Localized Inhibition Of Smooth Muscle Cell Proliferation, collected in *Discoveries in Radiation for Restenosis—Selected Literature* (Jan. 1996).

Waksman, et al., Intracoronary Radiation Before Stent Implantation Inhibits Neointima Formation In Stented Porcine Coronary Arteries, collected in *Dixcoveries in Radiation for Restenosis—Selected Literature* (Jan. 1996).

Hehrlein, et al., Low–Dose Radioactive Endovascular Stents Prevent Smooth Muscle Cell Proliferation And Neointimal Hyperplasia In Rabbits, collected in *Discoveries in Radiation for Restenosis—Selected Literature* (Jan. 1996).

Katzen, Mechanical Approaches To Restenosis In The Peripheral Circulation, collected in *Discoveries in Radiation for Restenosis—Selected Literature* (Jan. 1996).

Liermann, et al., Prophylactic Endovascular Radiotherapy To Prevent Intimal Hyperplasia After Stent Implantation In Femoropopliteal Arteries, collected in *Doscoveries in Radiation for Restenosis—Selected Literature* (Jan. 1996).

Wagner, et al., Potential Biological Effects Following High X–Ray Dose Interventional Procedures, collected in *Discoveries in Radiation for Restenosis—Selected Literature* (Jan. 1996).

Johnson, et al., Review Of Radiation Safety In The Cardiac Catherization Laboratory, collected in *Discoveries in Radiation for Restenosis—Selected Literature* (Jan. 1996).

Weintraub, et al., Can Restenosis After Coronary Angioplasty Be Predicted From Clinical Variables? collected in *Discoveries in Radiation for Restenosis—Selected Literature* (Jan. 1996).

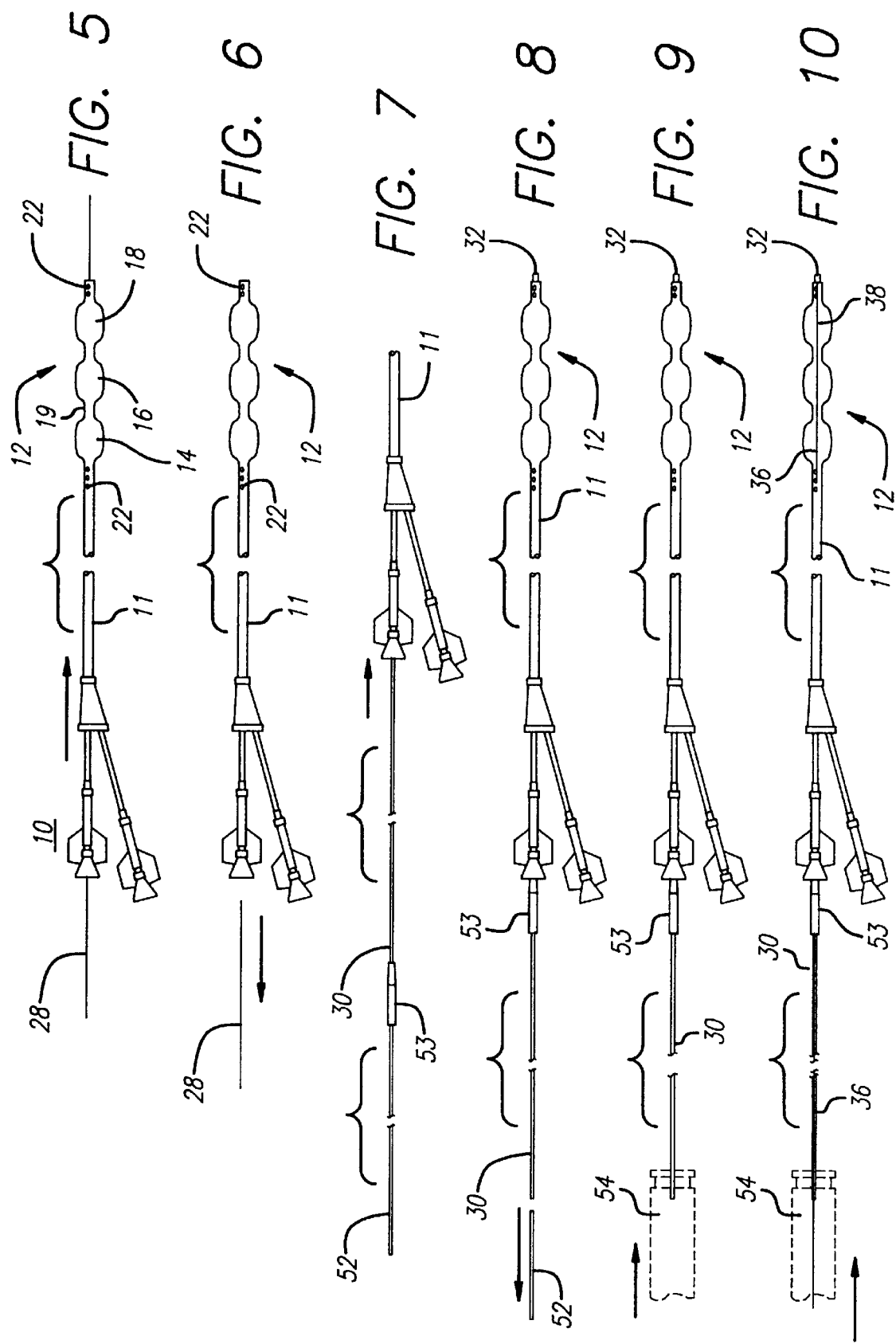

DEVICE FOR LOADING AND CENTERING A VASCULAR RADIATION THERAPY SOURCE

BACKGROUND OF THE INVENTION

This invention generally relates to intravascular catheters suitable for maintaining the patency of a body lumen during delivery of a radiation source to the body lumen. In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guide wire and a dilatation catheter having an inflatable balloon on the distal end thereof are introduced through the guiding catheter with the guide wire slidably disposed within an inner lumen of the dilatation catheter. The guide wire is first advanced out of the distal end of the guiding catheter and is then maneuvered into the patient's coronary vasculature containing the lesion to be dilated, and is then advanced beyond the lesion. Thereafter, the dilatation catheter is advanced over the guide wire until the dilatation balloon is located across the lesion. Once in position across the lesion, the balloon of the dilatation catheter is filled with radiopaque liquid at relatively high pressures (e.g., greater than about four atmospheres) and is inflated to a predetermined size (preferably the same as the inner diameter of the artery at that location) to radially compress the atherosclerotic plaque of the lesion against the inside of the artery wall to thereby dilate the lumen of the artery. The balloon is then deflated so that the dilatation catheter can be removed and blood flow resumed through the dilated artery.

After an angioplasty procedure, restenosis at or near the site of the original stenosis in the artery occasionally occurs. The smooth muscle cells of the artery may proliferate at the site of angioplasty treatment. Restenosis may result in a reformation of the lesion and a narrowing of the artery at the site.

Various devices and methods for the prevention of restenosis have been developed, including the use of an expandable stent on the distal end of the catheter designed for long-term implantation in the body lumen. Other devices and methods for the prevention of restenosis after angioplasty or another arterial intervention procedure employ a radiation source delivered through a balloon. The radiation operates to destroy the proliferating cells thereby preventing development of restenosis.

There is a need in the art for a catheter with a minimal profile having an expandable region which can maintain the patency of an artery and allow delivery of a radiation source to the treatment area for a period of time sufficient to prevent development of restenosis. Such an intravascular catheter should be easy and inexpensive to manufacture, have an expandable region that is strong and reliable under pressure, and be capable of forming a variety of shapes to allow flexibility in the amount and pattern of expansion and deformation of the expandable region. Further, the associated radiation source should be protected from any contact with the body fluids of the patient in order to allow the radiation source to be reused. The present invention fulfills these needs.

SUMMARY OF THE INVENTION

The invention is directed to an intravascular catheter with an expandable balloon located at the distal end of the catheter body which can hold a body lumen open for a period of time sufficient to permit delivery of a radiation source to a body lumen while permitting perfusion of blood. In one embodiment, the catheter comprises a catheter body having a proximal end and a distal end; an inflation region disposed at the distal end of the catheter body, the inflation region having at least two lobes, wherein the lobes are adapted to contact the body lumen when the lobes are inflated; and the catheter body further including an internal lumen extending from the proximal end of the catheter body, and adapted to receive a radiation source wire at the proximal end for delivery to the inflation region; wherein inflation of the lobes in the inflation region centers the radiation source wire within the body lumen.

A method of maintaining the patency of a body lumen and delivering radiation to the body lumen comprises the steps of introducing a catheter having a proximal end and a distal end to a treatment site in the body lumen; expanding an inflation region disposed at the distal end of the catheter, the inflation region having at least two lobes; loading a radiation source wire having a radiation source at the distal end of the radiation source wire into an internal lumen in the catheter; advancing the distal end of the radiation source wire to the inflation region, so that the radiation source is centered within the body lumen and substantially equal amounts of radiation energy are directed to the body lumen while the inflation region is expanded; and maintaining the radiation source at the inflation region for an adequate time so as to deliver a therapeutically significant radiation dose to the treatment site.

In one aspect of an embodiment of the catheter, multiple balloons are inflated so as to center the radiation source within the body lumen, especially where the body lumen is curved.

In another aspect of an embodiment of the invention, the internal lumen of the catheter is a blind lumen having a distal end which is not open to the body. The radiation source is delivered through the blind lumen so as to prevent contamination of the radiation source during treatment.

In another aspect of an embodiment of the invention, the catheter includes a delivery lumen adapted to receive either a guide wire or the blind internal lumen. The catheter body should have a small minimum profile.

In another aspect of an embodiment of the invention, the catheter further includes perfusion holes to allow blood flow while the balloons are inflated.

These and other aspects of the invention will become more apparent from the following detailed description in conjunction with the accompanying exemplary drawings.

BRIEF DESCRIPTION OF THE DRAWINGS

FIG. 3 is a cross-sectional view of the catheter with the radiation source wire loaded in the internal lumen, and the multiple balloon lobes of the catheter are inflated within a curved section of an artery to center the radiation source wire.

FIG. 5 is an elevational view of one embodiment of an intravascular catheter illustrating the first step of FIG. 4 in accordance with the present invention.

FIG. 6 is an elevational view of the catheter of FIG. 5, illustrating the second step of FIG. 4 in accordance with the present invention.

FIG. 7 is an elevational view of the catheter of FIG. 5 illustrating the third step of FIG. 4 in accordance with the present invention.

FIG. 8 is an elevational view of the catheter of FIG. 5 illustrating the fourth step of FIG. 4 in accordance with the present invention.

FIG. 9 is an elevational view of the catheter of FIG. 5 illustrating the fifth step of FIG. 4 in accordance with the present invention.

FIG. 10 is an elevational view of the catheter of FIG. 5 illustrating the sixth step of FIG. 4 in accordance with the present invention.

DETAILED DESCRIPTION OF THE PREFERRED EMBODIMENTS

The present invention provides a catheter which is adapted to deliver a low dose radiation source to a body lumen, such as a coronary artery, for an extended period of time. The catheter permits perfusion of blood during the radiation therapy and will center the radiation source so that equal amounts of radiation are applied to the artery. While the catheter is described in detail as applied to the coronary arteries, those skilled in the art will appreciate that the catheter can be used in other body lumens as well, including peripheral arteries and veins. Where different embodiments have like elements, like reference numbers have been used.

Figure 1:
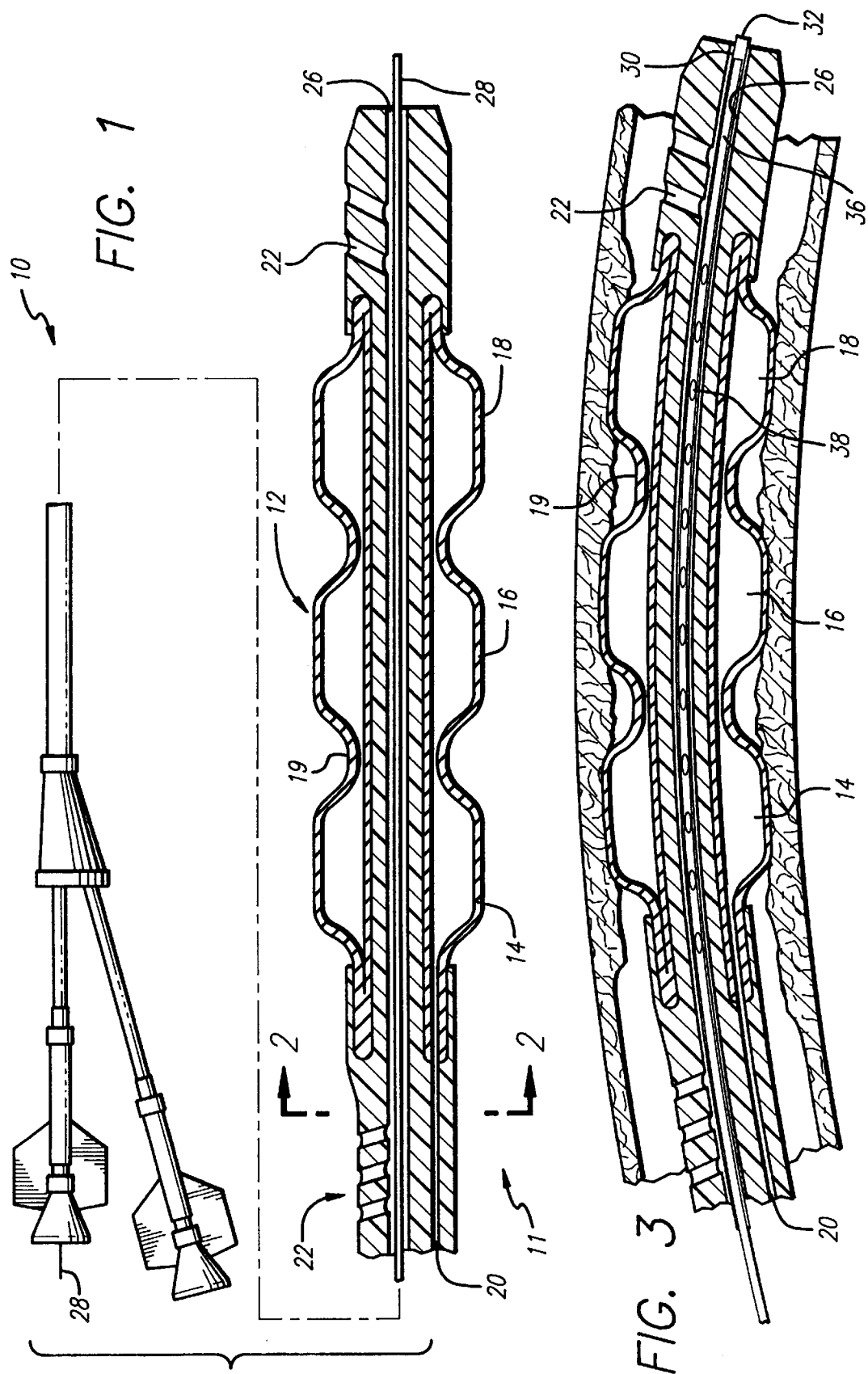
FIG. 1 is an elevational view, partially in crosssection, of an intravascular catheter embodying features of the present invention.

An embodiment of the intravascular catheter assembly 10, as shown in FIG. 1, includes an elongated catheter body 11, and an expandable inflation region 12 at the distal end of the catheter body. The inflation region 12 can be constructed of a single, multi-lobed balloon, or of multiple individual balloons. The inflation region 12 includes a first balloon lobe 14, a second balloon lobe 16, and a third balloon lobe 18 arranged adjacent to one another. The balloon lobes can be elastic or inelastic. Where the balloon lobes are inelastic, the lobes preferably inflate to approximately the same diameter. The balloon lobes are preferably spaced apart by relatively uninflatable or unexpandable regions 19. Multiple balloon catheters are described in U.S. Pat. Nos. 5,002,532 and 5,415,625 which are hereby incorporated by reference. The balloon lobes 14, 16, and 18 can be individual balloons which are separately inflatable, or the lobes can be part of a single, multi-lobed balloon. The lobes can be inflated by a single inflation lumen 20 or by multiple individual inflation lumens. Once the catheter assembly is properly positioned at the treatment site in the patient's vasculature, the balloon lobes at the inflation region are inflated. The triple-lobe balloon configuration allows the distal end of the catheter body to remain along a selected axis relative to the artery even when the artery is curved.

The catheter further includes a delivery lumen 26 extending through the catheter body 11. The catheter assembly 10 can be delivered to a treatment site over a guide wire 28 through the delivery lumen. The guide wire 28 includes a core member, and a helical coil or other flexible body disposed about and fixed to the distal portion of the core member. A rounded plug of radiopaque material is typically provided at the distal tip of the coil.

Perfusion holes 22 are formed at the distal end of the catheter body in order to allow blood flow in the artery while the balloon lobes are inflated. Blood enters the perfusion holes 22 which lead to the delivery lumen 26, and blood is carried back and through the delivery lumen. Blood entering the perfusion holes 22 at one side of the inflation region perfuses down the delivery lumen 26 alongside the guidewire, and exits the catheter through the distal end of the delivery lumen. Additional perfusion holes 22 can be formed in the catheter body at the opposite end of the inflation region to allow the blood to exit the delivery lumen 26. The perfusion holes are formed on the side wall of the catheter body, and can be cut in the form of notches. Perfusion dilation catheters are described in U.S. Pat. Nos. 4,790,315 and 5,334,154 which are hereby incorporated by reference.

The catheter assembly can be formed from conventional materials of construction. The material forming the catheter body can be any metal or polymer with ductile properties which would be acceptable for the needs of intravascular devices. Specifically, the material chosen for the catheter body should have sufficient flexibility to easily advance and navigate through tortuous anatomy.

The dimensions of the catheter assembly 10 can be the same dimensions as vascular catheters used in angioplasty procedures. In one embodiment for use in the peripheral arteries, the overall length of the catheter assembly is about 100 to 175 centimeters (cm), and the working length of the catheter body is preferably about 125 cm. The outer diameter of the catheter body is preferably 2.21 millimeters (mm). The diameter of the catheter body is in the range from about 0.02 to 0.152 cm. The balloon lobes of the inflation region in the uninflated condition have approximately the same diameter as the catheter body. The balloon lobes preferably are inflated to a diameter of about five millimeters. Each balloon lobe preferably includes a substantially flat region having a length of about 1.5 cm when inflated. The inflation region 12 occupies about ten centimeters along the distal end of the catheter body. The diameter of delivery lumen 26 should be larger than the diameter of guide wire 28 to allow the catheter to be easily advanced and removed over the guide wire. Further, the diameter of the delivery lumen 26 should be closely sized to the diameter of the internal lumen 30 which is inserted into the delivery lumen after removal of the guide wire 28. The internal lumen preferably has a length of about 130 cm, an inner diameter of 1.37 mm, and an outer diameter of 1.22 mm. The radiation source wire and the guide wire preferably have a diameter of approximately 1.1 mm, although the radiation source wire and the guide wire need not have the same diameter. It is to be understood that the catheter assembly 10 can be constructed to have the proper dimensions and flexibility for use and placement in other arteries, including the coronary artery.

Figure 2:
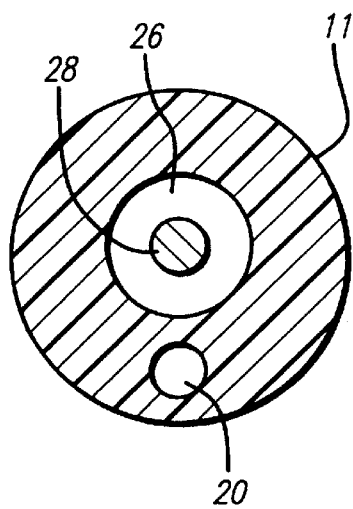
FIG. 2 is a cross-sectional view of the catheter of FIG. 1 taken along lines 2—2.

As shown in FIG. 2, the catheter body includes the inflation lumen 20, the perfusion channels 22, and the delivery lumen 26. The guide wire 28 occupies the delivery lumen 26 while the catheter is delivered to the treatment site. Once the catheter is in place, the guide wire 28 is removed, and the internal lumen 30 is inserted into the delivery lumen 26. The internal lumen is preferably inserted into the catheter by using a support mandrel removably inserted into the internal lumen 30 and pushing it distally into the delivery lumen 26. The internal lumen 30 is a blind (dead end) lumen sheath which is closed off at the distal end 32 to prevent entry of any body fluids such as blood into the internal lumen. The blind distal end 32 of the internal lumen 30 is placed at the inflation region 12 of the catheter. After the support mandrel is removed, a radiation source wire 36 is loaded into the blind internal lumen. The radiation source wire 36 is inserted into the blind lumen for a period of time sufficient to deliver the required radiation dose to the body lumen. The distal end of the radiation source wire 36 contains a radiation dose in the form of radiation pellets 38. The radiation source wire alternatively can contain radioactive gas, liquid or paste, or have a radioactive source coated on its distal end. Preferably, a low dosage of radiation is delivered to the artery or vessel. It is preferred that a dose level of about 0.1 to 4.0 curies is used. More preferably, a dose level of about 1.0 to about 2.0 curies is delivered to a coronary artery for a time sufficient to deliver from about 500 to about 3000 rads.

The radiation pellets 38 can be positioned at the appropriate location in the distal end of radiation source wire 36 to deliver the radiation dose. Inflation of the triple-lobe balloon centers the radiation source wire 36, and more specifically, the radiation pellets 38, within the artery so that uniform and equal amounts of radiation are applied to the artery wall during treatment. Centering the radiation source wire 36 in the artery can prevent the uneven application of radiation to the arterial wall. The internal lumen 30 containing the radiation pellets 38 of the radiation source wire 36 is preferably located along a central axis of the catheter body. It is understood, however, that the internal lumen can be located along any axis in the catheter body, so long as the radiation pellets or other radiation source is centrally located within the artery when the balloon lobes of the inflation region are inflated.

The distal portion of catheter assembly 10 is flexible where the inflatable balloon lobes 14, 16, and 18 are located, so that it can easily navigate a tortuous artery as the catheter assembly is advanced along the guide wire 28. The radiation source wire 36 should be centered within the artery even when the area where radiation is to be delivered is the curved portion of the artery. Accordingly, as shown in FIG. 3, the inflatable lobes are spaced apart in order to center the radiation source wire 36, even along the curved portion of the artery. The catheter body 11 is flexible, and it easily conforms to the curved portion of the artery. The inflation region 12 expands into contact with the artery, and centers the radiation source wire 36 and the radiation pellets 38 within the artery. The radiation pellets 38 should uniformly deliver a radiation dose, in equal amounts, to all portions of the affected artery.

Figure 4:
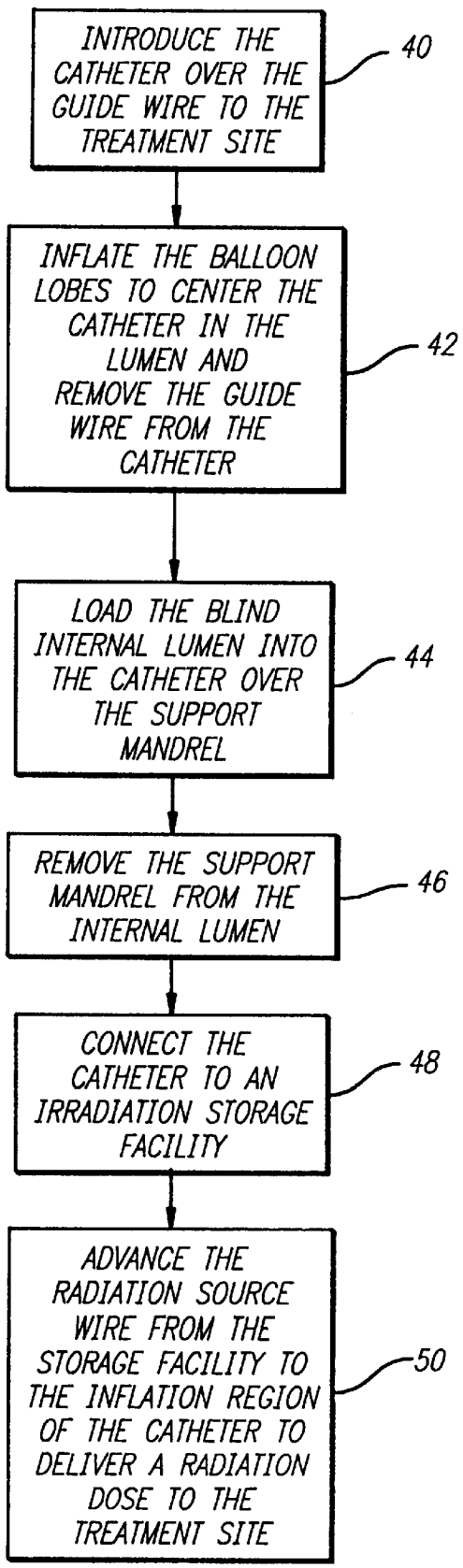
FIG. 4 is a flow chart describing the steps in a method of loading and centering the radiation source in a catheter in accordance with the present invention.

In one method of delivering a radioactive dose to a coronary artery in order to prevent restenosis, the catheter assembly is positioned across the portion of the arterial passageway where a previous PTCA, atherectomy procedure, laser ablation, or similar procedure was performed. The steps of the method, as shown in the flow chart of FIG. 4, will be discussed in connection with FIGS. 5–10.

In the introducing step 40, the catheter is introduced to the treatment site, such as the arterial site where an angioplasty procedure has been performed. The catheter assembly 10 can be back loaded over the guide wire 28, as shown in FIG. 5, which is already in place across the lesion from the previous PTCA procedure. The catheter should be situated so that the inflation region is located at the treatment site. The guide wire alternatively can be used in an over-the-wire arrangement or for a rapid-exchange-type of catheter. In a rapid-exchange arrangement, the proximal end of the guide wire is manually held while the rapid exchange catheter assembly is advanced over the guide wire to a desired location within the patient's artery, such as where a previous vascular procedure has been performed. A rapid exchange catheter is described in U.S. Pat. No. 5,458,613 which is hereby incorporated by reference. The catheter assembly in a rapid-exchange catheter includes a side wall port in the catheter body. The side wall port leads to the delivery lumen, or to a separate guide wire lumen. A small minimum profile for the catheter body can be maintained by having the side wall port lead into the delivery lumen instead of forming an entirely separate guide wire lumen.

In the inflating step 42, inflation of the balloon lobes holds open the artery at the treatment site, and centers the delivery lumen in the artery. The guide wire is then removed from the catheter assembly. As shown in FIG. 6, the guide wire 28 is removed through the proximal end of one embodiment of the catheter assembly 10. The perfusion holes allow blood to flow through the delivery lumen and past the inflation region while the balloon lobes are inflated.

In the loading step 44, once the inflation region is expanded, the blind internal lumen is loaded into the delivery lumen of the catheter assembly over the support mandrel. As shown in FIG. 7, the support mandrel 52 supports the blind internal lumen 30 during loading into the delivery lumen 26. The support mandrel 52 is rigid enough to prevent the blind internal lumen 30 from collapsing on itself during loading, and flexible enough to allow for external loading while the catheter is situated in the patient's vasculature. The internal lumen 30 is loaded so that the blind distal end 32 is adjacent to the distal end of the inflation region 12. The proximal end of the internal lumen includes a Luer fitting 53 to provide access for the radiation source wire into the catheter assembly through the internal lumen. It is to be understood that instead of a common Luer fitting 53, specialized custom fittings may be desirable to prevent accidental misconnections by ensuring that the various components are connectible only at their intended locations.

In the removing step 46, the support mandrel 52 is removed from the delivery lumen through the proximal end of the catheter assembly 10, as shown in FIG. 8. The Luer fitting 53 remains engaged with the port at the proximal end of the catheter assembly 10.

In the connecting step 48, the catheter is then connected to an irradiation storage facility which automatically loads the radiation source wire into the blind internal lumen. As shown in FIG. 9, the irradiation storage facility 54 is connected to the blind internal lumen of the catheter, and the physician activates the facility to advance and load a predetermined length of radiation source wire into the catheter assembly. The radiation source wire 36 from the storage facility 54 is inserted into the proximal end of the blind internal lumen through the Luer fitting 53.

In the advancing step 50, as shown in FIG. 10, the radiation source wire 36 is loaded into the internal lumen 30 until the distal end of the wire containing the radioactive source material reaches the blind distal end 32 of the internal lumen 30. The radiation source is positioned at the portion of the coronary artery which is to receive the radiation dose. The balloon lobes of the inflation region 12 are held in the expanded inflated condition for a sufficient amount of time to allow a therapeutically significant amount of radiation to treat the area and prevent restenosis. The inflation region 12, when expanded, presses against the walls of the artery and centers the radiation source wire 36 and the radiation source 38 relative to the walls of the artery. Centering the radiation dose allows all portions of the artery to receive uniform and equal amounts of radiation therapy.

After the radiation dose has been administered to the treatment area to prevent restenosis, the radiation source wire 26 can be removed from the catheter assembly and drawn back into the storage facility 54, and the inflation region 12 can be deflated and contracted. The catheter assembly 10 can then be withdrawn from the location within the patient's vasculature.

Other modifications can be made to the present invention without departing from the scope thereof. The specific dimensions, dosages, times, and materials of construction are provided as examples and substitutes are readily contemplated which do not depart from the invention. It will be recognized by those skilled in the art that the catheter assembly can be used within a patient's vasculature system after vascular procedures other than a PTCA or an atherectomy procedure. The scope of the invention should not be limited except as by the appended claims.

What is claimed is:

1. An intravascular catheter for maintaining the patency of a body lumen during delivery of radiation to the body lumen, the catheter comprising:

a catheter body having a proximal end and a distal end;

an inflation region disposed at the distal end of the catheter body, the inflation region having at least two lobes, the lobes adapted to contact the body lumen when inflated;

the catheter body further including a delivery lumen adapted to receive a guide wire for positioning the catheter body in the body lumen, the delivery lumen receiving an internal lumen after the guide wire is removed following the positioning of the catheter in the body lumen, the internal lumen adapted to receive a radiation source wire at the proximal end for advancement therein to the inflation region, whereby inflation of the lobes in the inflation region centers the radiation source wire within the body lumen.

2. The catheter of claim 1, wherein the internal lumen includes a closed distal end terminating at a point near the distal end of the inflation region, whereby the closed distal end of the internal lumen does not open to the body lumen so that the radiation source wire is not exposed to body fluids.

3. The catheter of claim 1, wherein the-catheter body further includes perfusion holes in fluid communication with the delivery lumen to permit perfusion of blood therethrough while at least one of the lobes is inflated.

4. An intravascular catheter for maintaining the patency of a body lumen during delivery of radiation to the body lumen, the catheter comprising:

a catheter body having a proximal end and a distal end;

an inflation region disposed at the distal end of the catheter body, the inflation region having at least two lobes, the lobes adapted to contact the body lumen when inflated;

a radiation source wire having a radiation source associated therewith;

the catheter body including an internal lumen extending from the proximal end of the catheter body to the inflation region the internal lumen receiving radiation source wire at the proximal end for advancement to the inflation region; and the catheter body further including a delivery lumen adapted to receive a guide wire for positioning the catheter body in the body lumen, and wherein the delivery lumen receives the internal lumen after the guide wire is removed following the positioning of the catheter body in the body lumens whereby inflation of the lobes of the inflation region when the radiation source wire is located within the inflation region centers the radiation source within the body lumen so that substantially uniform amounts of radiation energy is directed to all the surrounding walls of the body lumen.

5. The catheter of claim 4, wherein the catheter body includes perfusion holes in fluid communication with the blood flow and with the delivery lumen thereby permitting perfusion of blood while at least one of the lobes is inflated.

6. The catheter of claim 4, wherein the internal lumen includes a distal end terminating at a point near the distal end of the inflation region, wherein the distal end of the internal lumen does not open to the body lumen thereby preventing contamination of the radiation source wire.

7. The catheter of claim 4, wherein the lobes of the inflation region center the radiation source in the body lumen when the lobes are inflated, each lobe having a substantially flat area when inflated.

8. An intravascular catheter for maintaining the patency of a body lumen during delivery of radiation to the body lumen, the catheter comprising:

a catheter body having a proximal end and a distal end;

an inflation region disposed at the distal end of the catheter body, the inflation region having at least two lobes, the lobes adapted to contact the body lumen when inflated;

a radiation source wire having a proximal end and a distal end;

a radiation source located at the distal end of the radiation source wire; an internal lumen extending from the proximal end of the catheter body, the internal lumen having a distal end terminating at a point near the distal end of the inflation region, the internal lumen receiving a radiation source wire at the proximal end for advancement therein to the inflation region, wherein the distal end of the internal lumen does not open to the body lumen thereby preventing contamination of the radiation source wire; and a delivery lumen adapted to receive a guide wire, the catheter body advancing over the guide wire in the body lumen and wherein the delivery lumen is configured to receive the internal lumen after the guide wire is removed following positioning of the catheter body in the body lumen, whereby inflation of the lobes in the inflation region centers the radiation source within the body lumen so that a substantially uniform amount of radiation energy is directed to the surrounding walls of the body lumen.

9. The catheter of claim 8, wherein the catheter body includes perfusion holes in fluid communication with the blood flow and with the delivery lumen proximal of the inflation region, the delivery lumen in fluid communication with the body lumen distal of the inflation region thereby permitting perfusion of blood while at least one of the lobes is inflated.

10. The catheter of claim 8, wherein the radiation source delivers a low dosage of radiation to the body lumen at a position adjacent the distal end of the internal lumen.

11. The catheter of claim 8, wherein the inflation region is configured to center the radiation source within the body lumen so that a substantially uniform amount of radiation energy is directed to the surrounding walls of the body lumen.

12. The catheter of claim 8, wherein the lobes of the inflation region center the radiation source in the body lumen when the lobes are inflated, each lobe having a substantially flat region formed along the lobe when inflated.

13. A method of maintaining the patency of a body lumen and delivering radiation to the body lumen, the method comprising the steps of:

introducing a catheter having a proximal end and a distal end and a delivery lumen to a treatment site in the body lumen;

expanding an inflation region disposed at the distal end of the catheter, the inflation region having at least two lobes;

loading a radiation source wire having a distal end, and having a radiation source at the distal end thereof, into an internal lumen;

loading the internal lumen into the delivery lumen, the internal lumen having a closed distal end to prevent contamination of the radiation source wire;

advancing the distal end of the radiation source wire through the internal lumen to the inflation region so that the radiation source is centered within the body lumen and a substantially uniform amount of radiation energy is directed to the surrounding walls of the body lumen while the inflation region is expanded; and maintaining the radiation source at the inflation region for a time sufficient to deliver a therapeutically significant radiation dose to the treatment site in the body lumen.

14. The method of claim 13, wherein the step of introducing the catheter further includes the step of loading the catheter over a guide wire through the delivery lumen in the catheter, and the step of removing the catheter over the guide wire in the delivery lumen.

15. The method of claim 13, wherein the step of loading the internal lumen further includes the step of inserting a support mandrel into the internal lumen, and removing the support mandrel after the internal lumen has been properly positioned in the delivery lumen of the catheter.

16. The method of claim 13, further comprising the step of perfusion blood through perfusion holes formed in the catheter before the step of loading the internal lumen, the perfusion holes leading to the delivery lumen.

17. The method of claim 13, wherein the step of expanding the inflation region further includes the step of inflating the lobes of the inflation region through a single inflation lumen.

18. The method of claim 13, wherein the step of expanding the inflation region further includes the step of inflating the lobes of the inflation region to form a substantially flat region along each inflated lobe.

* * * * *